United States Patent [19]

Brown

[11] Patent Number: 4,695,273
[45] Date of Patent: Sep. 22, 1987

[54] MULTIPLE NEEDLE HOLDER AND SUBCUTANEOUS MULTIPLE CHANNEL INFUSION PORT

[75] Inventor: Eric W. Brown, Redondo Beach, Calif.

[73] Assignee: I-Flow Corporation, Torrance, Calif.

[21] Appl. No.: 849,408

[22] Filed: Apr. 8, 1986

[51] Int. Cl.⁴ .............................................. A61M 5/00
[52] U.S. Cl. .................................. 604/173; 604/175; 604/283; 604/244
[58] Field of Search ................. 604/175, 173, 93, 100, 604/264, 280, 283, 87, 206, 244, 257, 258

[56] References Cited

U.S. PATENT DOCUMENTS

| | | | |
|---|---|---|---|
| 3,572,336 | 3/1971 | Hershberg | 604/173 |
| 3,640,269 | 2/1972 | Delgado | 128/2 R |
| 3,682,087 | 8/1972 | Panek | 604/173 X |
| 3,783,868 | 1/1974 | Bokros | 128/260 |
| 3,949,746 | 4/1976 | Wallach | 604/173 |
| 3,964,482 | 6/1976 | Gerstel et al. | 128/260 |
| 4,193,397 | 3/1980 | Tucker et al. | 604/932 |
| 4,400,169 | 8/1983 | Stephen | 604/49 |
| 4,417,888 | 11/1983 | Cosentino et al. | 604/175 |
| 4,490,137 | 12/1984 | Moukheibir | 604/28 |
| 4,496,350 | 1/1985 | Cosentino | 604/175 |
| 4,543,088 | 9/1985 | Bootman et al. | 604/93 |
| 4,548,607 | 10/1985 | Harris | 604/891 |
| 4,557,722 | 12/1985 | Harris | 604/9 |
| 4,581,012 | 4/1986 | Brown et al. | 604/175 X |

OTHER PUBLICATIONS

Cormeditations, Sep. 1985, Issue No. 8.
MediPort, "Totally Implanted Vascular Access Device", Copyrighted 1983.
Port-A-Cath, "Totally Implantable Drug Delivery System", (Advertisement).

Primary Examiner—Stephen C. Pellegrino
Attorney, Agent, or Firm—Robert M. Asher

[57] ABSTRACT

A multiple needle holder and multiple channel subcutaneous infusion port are disclosed. The multiple needle holder carries a plurality of needles which are each in separate fluid communication with a lumen of a plurality of lumens in a multilumen catheter. The multiple infusion port includes a septum which overlies a plurality of isolated chambers. Each chamber is accessed by a tube which connects to a different lumen of a subcutaneous multilumen catheter. When the needles of said needle holder are inserted through the septum of said infusion port each of said needles is in communication with a different one of said isolated chambers.

13 Claims, 5 Drawing Figures

MULTIPLE NEEDLE HOLDER AND SUBCUTANEOUS MULTIPLE CHANNEL INFUSION PORT

BACKGROUND OF THE INVENTION

This invention relates to devices for providing infusions of a plurality of fluids repeatably to a patient. In particular, the invention relates to a multiple needle holder and subcutaneous multiple channel infusion port.

Implantable vascular access devices are well known in the art. A conventional implantable port includes a single reservoir having a catheter attached thereto. The catheter is fed into a blood vessel in a patient's body. Fluid injected into the reservoir of the implanted port flows through the catheter and into the blood stream. The infusion port is implanted beneath the skin of the patient. The top of the port has a septum which is penetrable by a hypodermic needle. Thus, conventional injections of medicament into a patient having an implanted port are made by inserting a needle through the patient's skin and through the septum in the infusion port. Fluid is injected through the needle and into the reservoir of the port where it passes into the catheter and out into the blood stream.

Experimentation and advances in medicine are creating new needs for infusing more than a single fluid into a patient. There are many applications for which there is a need for intravenous administration of a plurality of fluid solutions. One such application is the use of chemotherapy to treat such diseases as cancer. Attempts at providing more advanced chemotherapy regimens involving the intravenous administration of a multiplicity of drug solutions are being inhibited by a lack of equipment to simplify such a procedure. The use of implanted infusion ports for delivering drug solutions to a patient are desirable since they deliver the fluid solution directly into the blood stream where it is quickly delivered throughout the body.

A dual reservoir double lumen implantable vascular access port is presently available. This dual lumen implantable port made available by Cormed, Inc. of Medina, New York has two separate stainless steel reservoirs mounted in a silicone rubber base. Each reservoir is connected to an individual branch of a double lumen catheter. Each reservoir has its own septum through which a needle may be inserted to inject fluid into a patient. This dual lumen port has the limitation of only allowing for the injection of two fluids simultaneously. A further disadvantage of this device is that, when used for continuous infusion, two separate catheters would hang from the patient, each connected to one of two needles.

SUMMARY OF THE INVENTION

This invention is directed to a multiple needle holder adapted for engagement with a multilumen locking connector and a subcutaneous multiple channel infusion port.

According to the multiple needle holder of the present invention, a plurality of needles extend from the front face of a housing. At the rear of the housing are a plurality of inlet openings each opening provided in a separate engagement port. A flange extends from the housing for engagement with a locking ring on a multilumen locking connector. Each lumen of the multilumen connector engages one of the engagement ports at the rear of the housing of the needle holder. Each of the needles on the needle holder is in communication with an inlet opening at the rear of the housing. Thus, upon connection to a multilumen catheter each needle is in communication with one of the lumens of that catheter.

In accordance with the multiple channel subcutaneous infusion port of the present invention, the infusion port provides a plurality of isolated chambers. A penetrable septum overlies the isolated chambers. A multilumen catheter is connected to the infusion port and extends therefrom. Each lumen of the multilumen catheter is connected to a different one of the isolated chambers by a chamber access tube. Each isolated chamber is adjacent the inner surface of the septum such that a plurality of needles aligned in parallel can be inserted through the septum, each needle entering a different one of said isolated chambers.

It is an object of the present invention to provide a single implantable port which can be used in the injection of a plurality of fluid solutions. It is a further advantage of the present invention that it keeps each of the plurality of fluids solutions being injected into the port isolated from one another until the fluid reaches the blood stream. The present invention advantageously provides for infusion of a plurality of fluids into an implanted infusion port through the use of a single catheter and needle holding device.

Other objects and advantages of the invention will become apparent during the following description of the presently preferred embodiments of the invention taken in conjunction with the drawings.

DETAILED DESCRIPTION OF THE PREFERRED EMBODIMENTS

Figure 1:
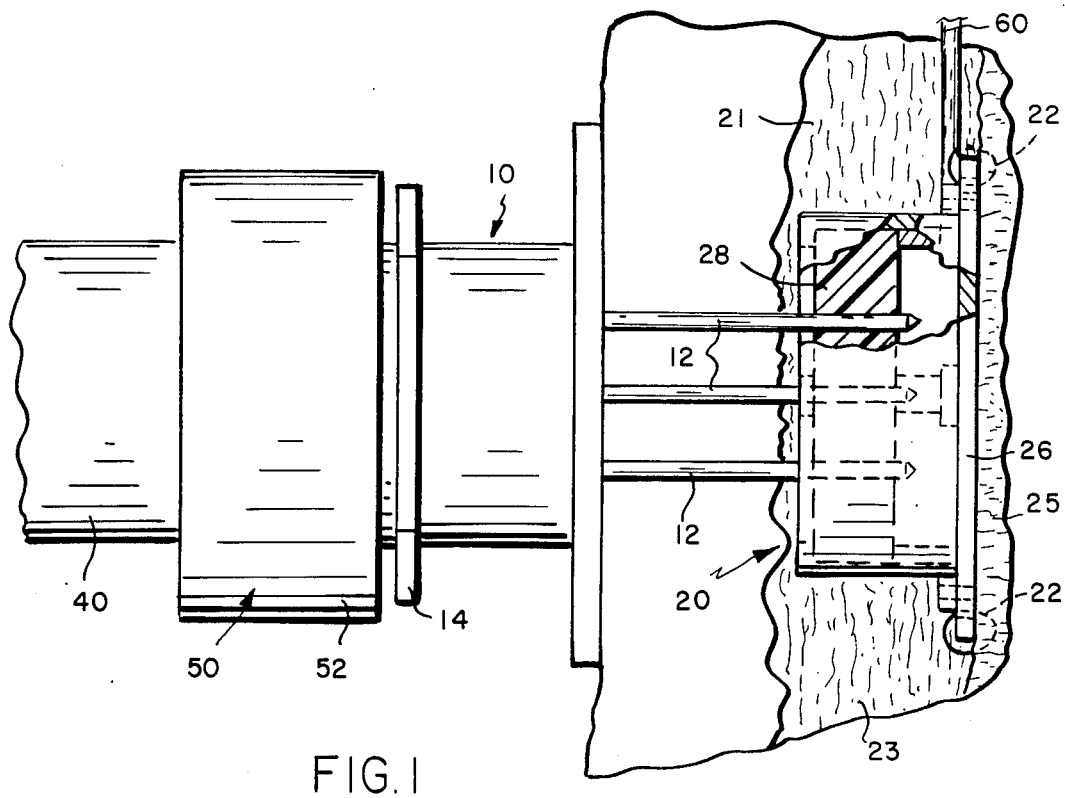
FIG. 1 is a plan view in partial cross-section of the needle holder and infusion port of the present invention as they would appear in use on a patient.

Referring now to the drawings, FIG. 1 shows a multiple channel needle holder 10 with its needles 12 inserted into a multiple channel subcutaneous infusion port 20. The infusion port 20 is implanted within the layer of fatty tissue 23 underneath the skin surface 21. Sutures 22 hold the infusion port to the muscle wall 25 beneath the fatty tissue. The sutures 22 are applied through slots 24 distributed around the edge portion of a base 26 of the infusion port 20. The needles 12 penetrate septum 28 at the top portion of the infusion port and extend through into a plurality of isolated chambers 30. The drawings show a needle holder and multichannel infusion port with four needles and isolated chambers respectively, however, it should be understood that the invention is not limited to any specific number of needles or chambers.

The needle holder 10 is shown attached to a multilumen catheter 40 by a multilumen locking connector 50. A multilumen locking connector which may be used in conjunction with the needle holder of the present invention is described in allowed U.S. patent application Ser.

No. 678,481, filed Dec. 5, 1984 which will issue as U.S. Pat. No. 4,581,012 on Apr. 8, 1986 and sharing the same Assignee as the present invention. The disclosure of said patent is hereby incorporated by reference herein. As shown in FIG. 1, the locking connector 50 includes a locking ring 52 which engages a flange 14 on the outside of the housing of the needle holder 10. FIG. 1 shows the locking ring 52 prior to engagement with the flange 14.

In operation, individual fluid solutions are passed through each lumen of the multilumen catheter 40 into the needle holder 10 where they are injected through the needles 12 into the isolated chambers 30 of the infusion port 20. The fluids continue out of the infusion port 20 through a subcutaneous multilumen catheter 60. Each fluid solution thus remains isolated from each of the other fluid solutions until it reaches the blood stream at the end of the catheter 60.

Figure 2:
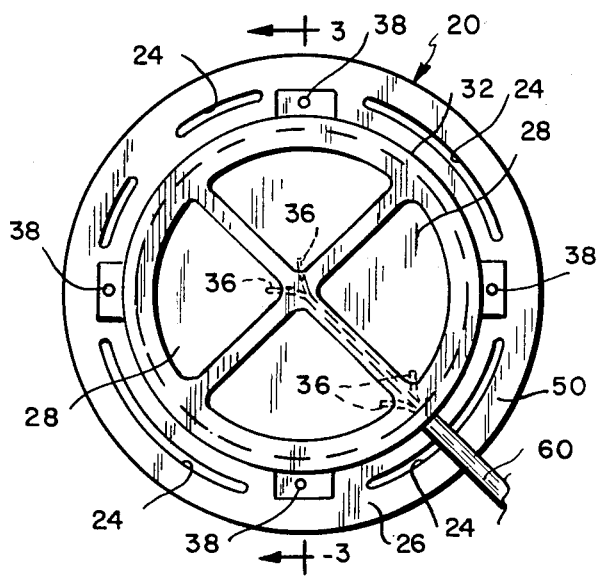
FIG. 2 is a top view of the multiple channel subcutaneous infusion port of the present invention.
Figure 3:
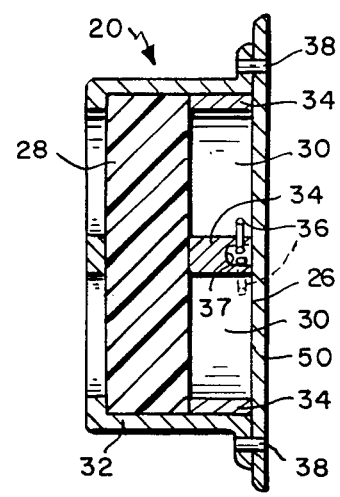
FIG. 3 is a side view of the infusion port of FIG. 2.

Referring now to FIGS. 2 and 3, the multichamber subcutaneous infusion port is discussed in greater detail. The housing of the port includes a housing wall 32 resting upon the base 26 of the port. Located within the housing are sealing walls 34 which isolate each chamber 30 from one another and a septum 28 which overlies the sealing walls 34 to enclose the chambers 30. A silicon gasket may be placed between sealing walls 34 and base 26 to aid in sealing the chambers. The housing wall 32, base 26 and sealing walls 34 are preferably made out of stainless steel. The inner face of the septum 28 is adjacent the chambers 30 and is on the opposite side of the septum from an outer face which is exposed through the top of the housing. The septum 28 is made of a penetrable self sealing material, typically silicone. A multilumen catheter 60 is connected to the infusion port 20 through a hole in the housing. Each lumen of the multilumen catheter is in communication with a chamber access tube 36. There is a chamber access tube 36 for each lumen. Each chamber access tube 36 is in communication with a different one of the isolated chambers 30 for conducting fluid out its respective chamber. In the preferred embodiment shown, the hole in the housing is adjacent two chambers 30. The access tubes 36 for these chambers feed immediately into the multilumen catheter 60. A conduit 37 through a sealing wall 34 provides space for the two other access tubes 36 which extend into their respective chamber 30 near the center of the infusion port 20.

In the preferred embodiment, press fit assembly pins 38 hold the housing wall 32 to the base 50. The top portion of the housing 32 holds the septum 28 in place over the sealing walls 34. The top portion of the housing can be shaped as the sealing walls 34 to provide solid portions over the sealing walls and openings superimposed over said chambers so that a needle injected into the septum 28 will be inserted into a chamber 30 rather than a sealing wall 34. Slots 24 are provided about the periphery of the base 50. Sutures may be applied through the slots to hold the infusion port in place within the patients body.

Figure 4:
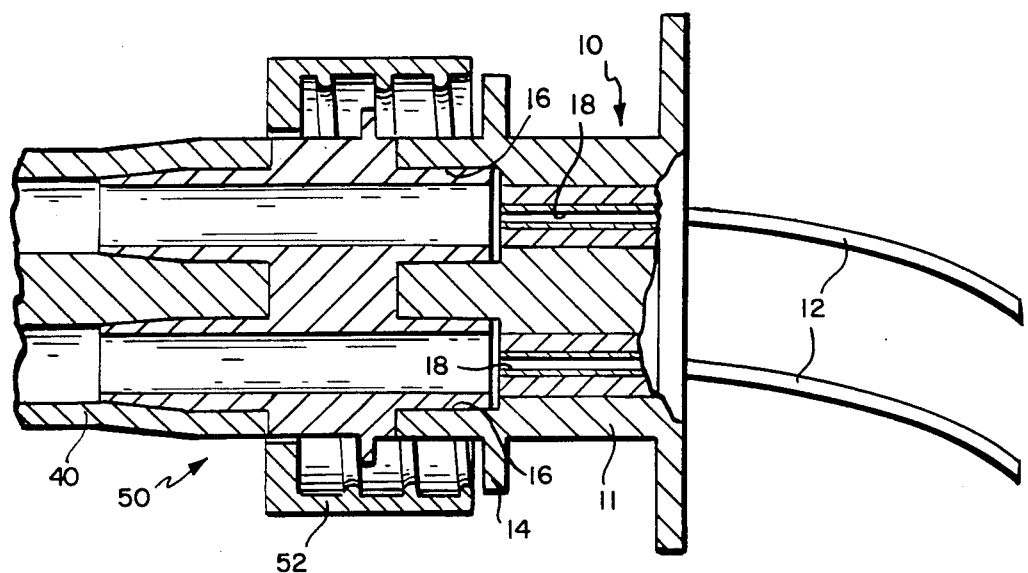
FIG. 4 is a cross-sectional view of the needle holder of the present invention and a multilumen locking connector.
Figure 5:
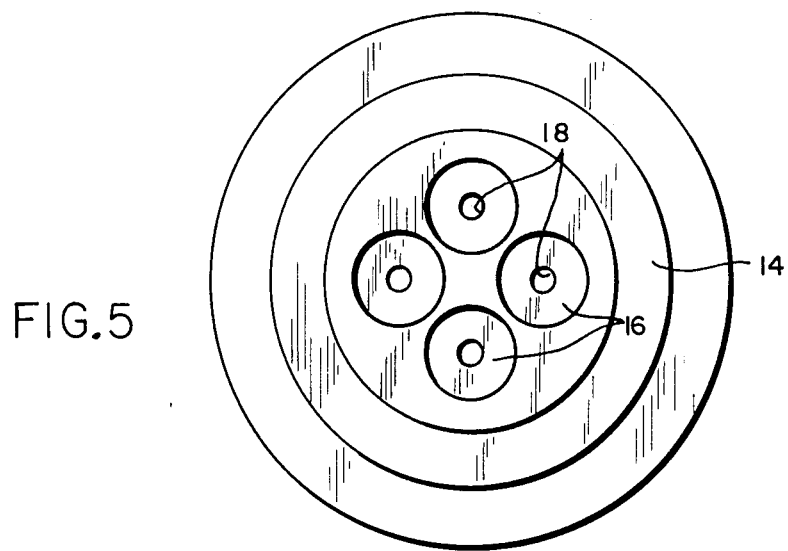
FIG. 5 is a rear plan view of the needle holder of the FIG. 4.

The needle holder 10 of the present invention shall now be described with reference to FIGS. 4 and 5. The needle holder 10 of FIG. 4 is shown with curved needles 12. The needle holder is made with a housing 11, preferably made from plastic. Curved needles are an alternative to the straight needles shown in FIG. 1. Curved needles advantageously hold more securely onto an infusion port. The needles 12 are secured within the housing 11 by a conventional bonding technique, such as gluing or potting. The insertion end of the needles extend out from the front face of the housing 11. The needles 12 are in fluid communication with the inlet openings 18 at the rear face of the housing 11. Each of the openings 18 is located within an engagement port 16. In the embodiment shown the engagement port 16 are female connectors for engagement with the male connectors of a multilumen catheter connector 50. It would be equally possible to interchange this arrangement and provide male engagement ports 16 on the needle holder 10 and female connectors on the multilumen catheter connector 50. A flange 14 extends from the needle holder 10 for engaging the multilumen locking connector 50. As shown in FIG. 4, the multilumen locking connector 50 includes a locking ring 52 which has a threaded interior. The threaded interior engages the flange 14 and allows the connector to be screwed tightly onto the needle holder. The combination of multilumen catheter 40, multilumen catheter connector 50 and needle holder 10 provide four individual passageways for four separate fluid solutions.

The needle holder may be changed so that the front face and rear face of the needle holder housing are perpendicular to each other. This would advantageously allow the external catheter 40 to lie flat against a patient's body when the needle holder 10 is inserted into the infusion port 10.

Of course, it should be understood that various other changes and modifications to the preferred embodiments described above will be apparent to those skilled in the art. For example, the subcutaneous catheter can be connected to the infusion port through the base instead of the housing. This and other changes can be made without departing from the spirit and the scope of the invention and without diminishing its attendent advantages. It is therefore intended that such changes and modifications be covered by the following claims:

I claim:

1. A multiple needle holder comprising:
   a housing having a housing wall surrounding a plurality of conduits extending from a rear face on said housing to a front face;
   a plurality of needles secured within said housing so that each of said needles is in communication with one of the said conduits, said needles extending outwards from the front face of said housing;
   a plurality of engagement ports on the rear face of said housing each having an opening in communication with one of said conduits, said engagement ports being arranged so as to be matingly aligned with a plurality of ports on a multilumen catheter connector; and
   means extending outwardly from said housing wall for engaging a locking mechanism.

2. The needle holder of claim 1 wherein said means for engaging a locking mechanism comprises a flange extending outwardly from said housing wall.

3. The needle holder of claim 1 wherein each of said plurality of needles is curved.

4. The needle holder of claim 1 wherein the rear face of said housing is perpendicular to the front face of said housing.

5. A multiple channel infusion port comprising:
   a housing including a housing wall and a base;
   a penetrable self-sealing septum held within said housing and having an outer face adjacent at least one opening in said housing and an inner face on the opposite side of said septum from said outer face;

a plurality of isolated chambers adjacent the inner face of said septum;

a sealing wall separating each of said isolated chambers from one another; and a plurality of access tubes each in communication with one of said isolated chambers for conducting fluid out of the isolated chambers.

6. The mutliple channel infusion port of claim 5 further comprising a multilumen catheter, each lumen of said catheter being in communication with one of said access tubes.

7. The multiple channel infusion port of claim 5 further comprising slot means in the base of said housing for enabling sutures to be applied therethrough.

8. The multiple channel infusion port of claim 5 wherein said housing includes a top portion having solid portions overlying said sealing wall and openings superimposed over said chambers.

9. A multiple needle holder and infusion port comprising:

a housing having a rear face and a front face, a plurality of needles secured within said housing and extending from the front face of said housing;

a plurality of engagement ports on the rear face of said housing each having an opening in communication with one of said needles; and an infusion port having a plurality of isolated chambers beneath a self-sealing septum such that when the needles of said needle holder penetrate through said septum each needle is in communication with a different one of said chambers.

10. The multiple needle holder and infusion port of claim 9 wherein said infusion port includes a plurality of access tubes each in communication with one of said isolated chambers for conducting fluid out of the isolated chambers.

11. The multiple needle holder and infusion port of claim 10 further comprising a multilumen catheter, each lumen of said catheter being in communication with one of said access tubes.

12. The multiple needle holder and infusion port of claim 9 further comprising slot means on said infusion port for enabling sutures to be applied therethrough.

13. The multiple needle holder and infusion port of claim 9 wherein the rear face of said housing is perpendicular to the front face of said housing.

* * * * *